United States Patent [19]
Lee et al.

[11] Patent Number: 5,952,218
[45] Date of Patent: Sep. 14, 1999

[54] CONTAINER HOLDER REFLECTANCE FLAG

[75] Inventors: Gregory S. Lee, Oklahoma City; William Adcox, Lexington; Lanny V. Grade, Oklahoma City, all of Okla.

[73] Assignee: Akzo Nobel, N.V., Arnhem, Netherlands

[21] Appl. No.: 09/053,905

[22] Filed: Apr. 2, 1998

[51] Int. Cl.$^6$ .................................................. C12M 1/34
[52] U.S. Cl. ..................... 435/288.7; 435/808; 435/809; 422/82.06; 422/82.07; 422/104; 250/252.1; 250/328; 250/574; 250/576; 356/440; 356/445; 211/74; 248/311.2
[58] Field of Search ............................. 435/286.2, 287.3, 435/287.5, 287.9, 288.1, 288.7, 808, 809; 422/82.05, 82.06, 82.07, 82.08, 104, 64, 65; 250/252.1, 328, 574, 576, 428, 432 R, 458.1, 461.1, 484.4; 356/440, 445, 446, 448; 248/311.2, 313, 316.1, 316.7, 316.8; 211/74, 60.1

[56] References Cited

U.S. PATENT DOCUMENTS

| | | |
|---|---|---|
| 3,186,556 | 6/1965 | Forsstrom . |
| 3,286,583 | 11/1966 | Ferrari . |
| 3,522,436 | 8/1970 | Posgate . |
| 3,544,225 | 12/1970 | Wattenburg et al. . |
| 3,551,062 | 12/1970 | Brown . |
| 3,941,237 | 3/1976 | MacGregor, Jr. . |
| 4,936,682 | 6/1990 | Hoyt . |
| 4,945,060 | 7/1990 | Turner et al. . |
| 5,074,505 | 12/1991 | DiGuiseppi et al. . |
| 5,094,955 | 3/1992 | Calandra et al. . |
| 5,162,229 | 11/1992 | Thorpe et al. . |
| 5,164,796 | 11/1992 | DiGuiseppi et al. . |
| 5,217,876 | 6/1993 | Turner et al. . |
| 5,518,923 | 5/1996 | Berndt et al. . |
| 5,700,429 | 12/1997 | Buhler et al. . |
| 5,796,486 | 8/1998 | Jacob . |

*Primary Examiner*—William H. Beisner
*Attorney, Agent, or Firm*—Gregory R. Muir

[57] ABSTRACT

A bottle retaining mechanism holds a culture bottle in place in a cell in an incubating apparatus which agitates the culture bottle and detects the growth of microorganisms in the culture bottle. When a bottle is not present in the cell of the apparatus, the retaining mechanism moves to a position which reflects light from the light emitter to the light detector in an amount greater than the amount of light reflected off of a bottle when present, so as to indicate when a bottle is not present in a cavity of the bottle holder. The retaining mechanism/reflectance flag also is capable of providing a reference signal for auto-calibration purposes. The amount of light reflected from the retaining mechanism/reflectance flag to the light detector in a cell when no bottle is present can be monitored in order to detect changes in the cell. By monitoring such changes in the empty cell, drift from the original cell calibration can be monitored. Based on the magnitude of the measured changes, small changes could be compensated for, whereas large changes could indicate that a cell must be replaced.

17 Claims, 6 Drawing Sheets

CONTAINER HOLDER REFLECTANCE FLAG

BACKGROUND OF THE INVENTION

In the field of culturing and detecting microorganisms, specialized culture bottles and machines for holding the culture bottles are used for detecting the presence of microorganisms in a test specimen. Bottles, such as those disclosed in U.S. Pat. Nos. 4,945,060; 5,094,955; and 5,162,229 have a culture medium and a sensor in the interior of the bottle that undergoes a detectable change due to the growth of microorganisms present in the bottle. The change in the sensor is monitored from outside the culture bottle through the transparent wall of the culture bottle, such as with a light emitter and detector as disclosed in, for example, U.S. Pat. Nos. 5,164,796 and 5,217,876. For most assays, the culture bottles should be agitated for best results. Clips, such as those disclosed in U.S. Pat. No. 5,074,505, can hold the culture bottles in place in the incubating machine during agitation. All of the above-mentioned patents are incorporated herein in their entirety by reference.

SUMMARY OF THE INVENTION

In the present invention, a bottle retaining mechanism is provided for holding a culture bottle in place in a cell in the incubating apparatus. As used herein, "bottle" denotes any container, and in a preferred embodiment, any container that might be used for culturing microorganisms. When a bottle is not present in a respective bottle holder in the apparatus, the retaining mechanism moves to a position that allows for reflecting light from the light emitter to the light detector in an amount greater than the amount of light reflected from a bottle when present. As such, the retaining mechanism also acts as a reflectance flag and indicates when a bottle is not present in a bottle holding cavity of the incubating apparatus.

The reflectance flag also is capable of providing a reference signal for auto-calibration. The amount of light reflected from the retaining mechanism/reflectance flag to the light detector in a cell when no bottle is present can be monitored in order to detect changes in the cell. By monitoring such changes in the empty cell, drift from the original cell calibration can be determined. Compensation can be made for small changes, whereas large changes could indicate that a cell must be replaced.

BRIEF DESCRIPTION OF THE DRAWINGS

A preferred embodiment of the invention will be described in conjunction with the accompanying drawings, wherein.

DETAILED DESCRIPTION OF THE PREFERRED EMBODIMENTS

Figure 1:
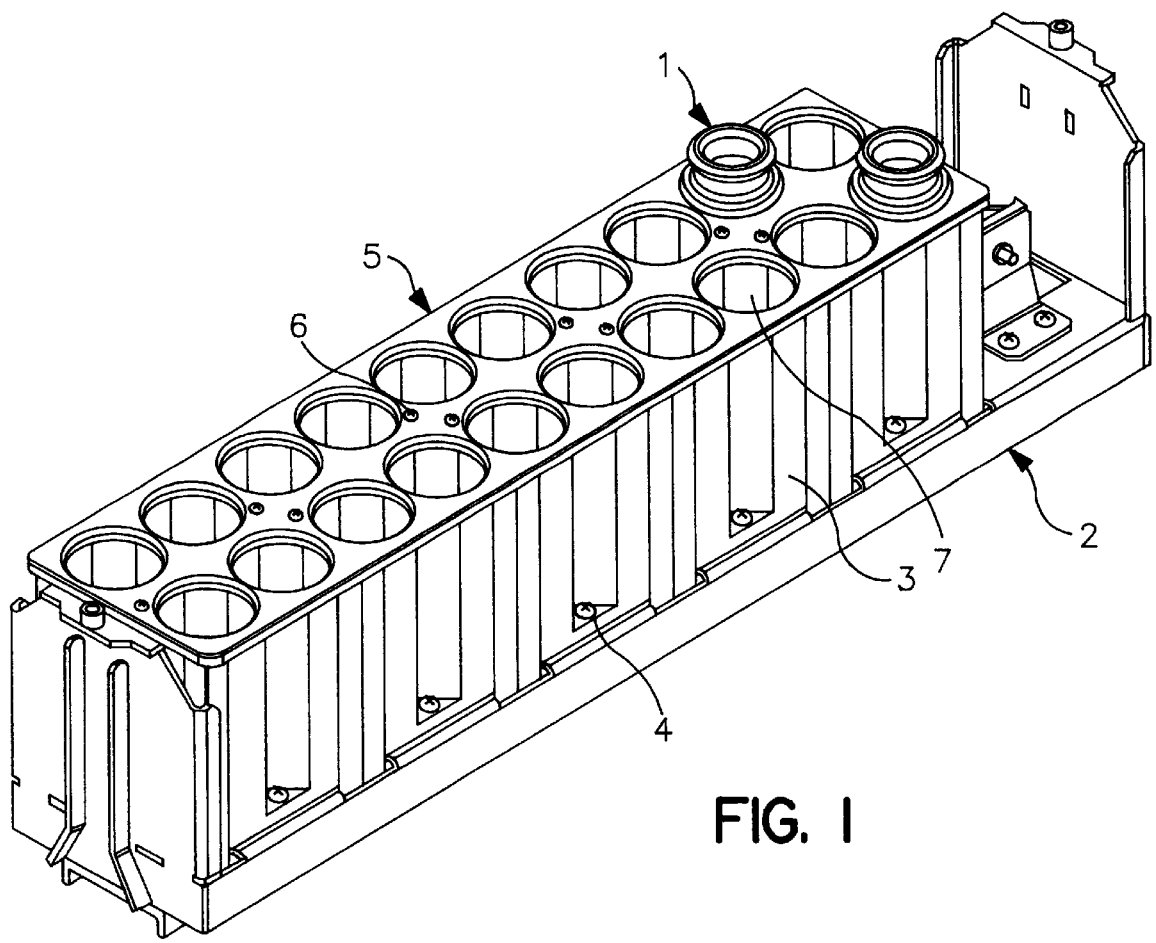
FIG. 1 is an illustration of a rack with bottle holders for holding culture bottles.

FIG. 1 is an illustration of a rack for holding a plurality of culture bottles. As can be seen in this figure, a rack 2 is provided, on which are mounted a plurality of bottle holders 3 having an internal elongated cavity 7 for holding a culture bottle. The bottle holders 3 are held on rack 2 by, for example, screws 4. A top plate 5 is mounted on top of the plurality of bottle holders 3 via screws 6, for example. A culture bottle 1 is shown being held within one of the cavities of one of the bottle holders.

Figure 2:
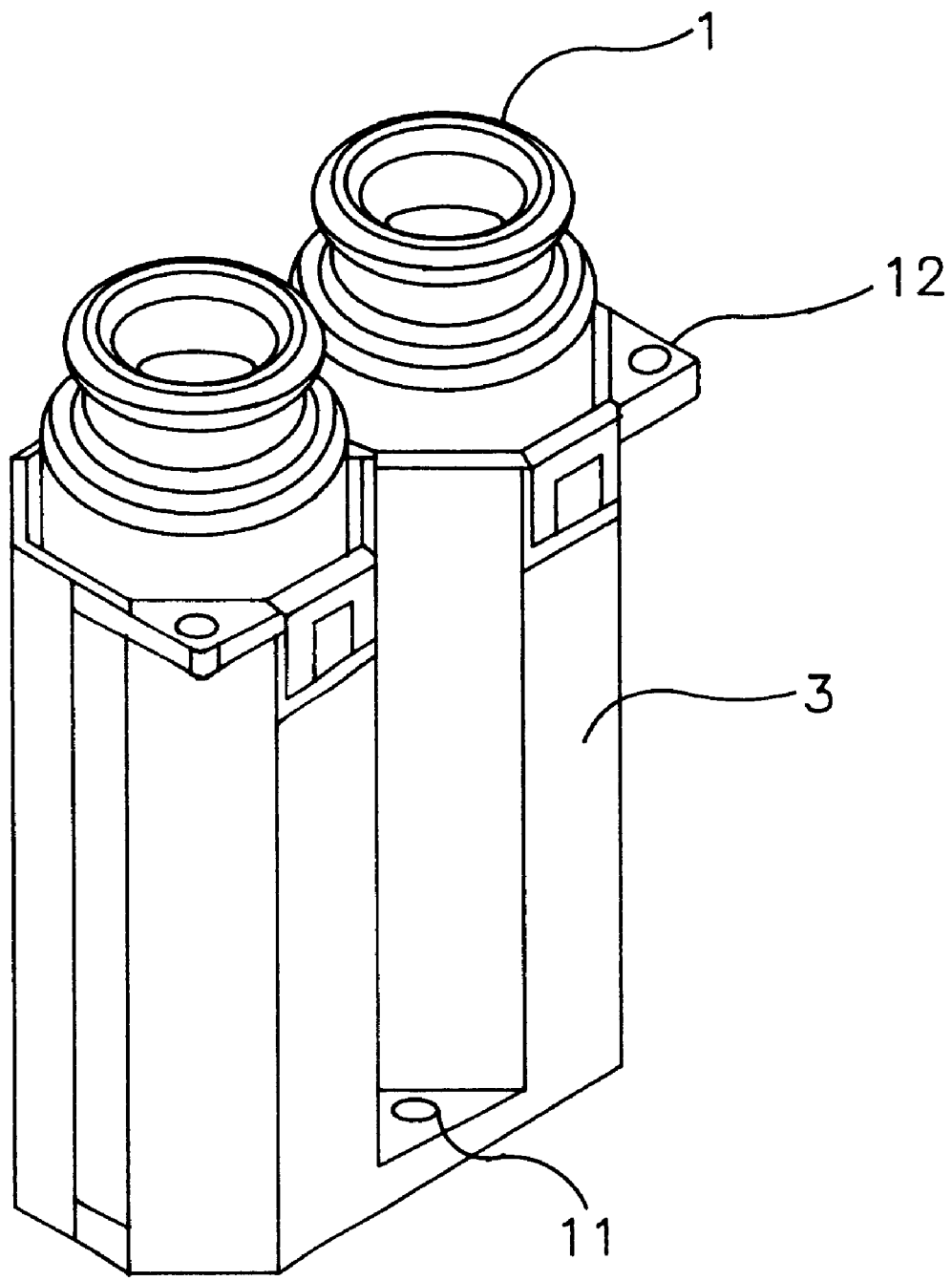
FIG. 2 is an illustration of a bottle holder holding two bottles therein.

As can be seen in FIG. 2, one example of a bottle holder is capable of holding two culture bottles 1. The bottle holder has at least one bottom screw hole 11 for attaching the bottle holder to the rack. The bottle holder is also provided with at least one top screw hole 12 for attaching the cover plate. Of course many other attachment mechanisms could be used, including welding/friction welding the parts together, clips, ties, clamps, etc. Also, though the bottle holder 3 illustrated is for holding two bottles, the bottle holder could easily be constructed for holding a single bottle, or for holding more than two bottles, or constructed as an integral unitary structure with the rack and/or top plate.

Figure 3:
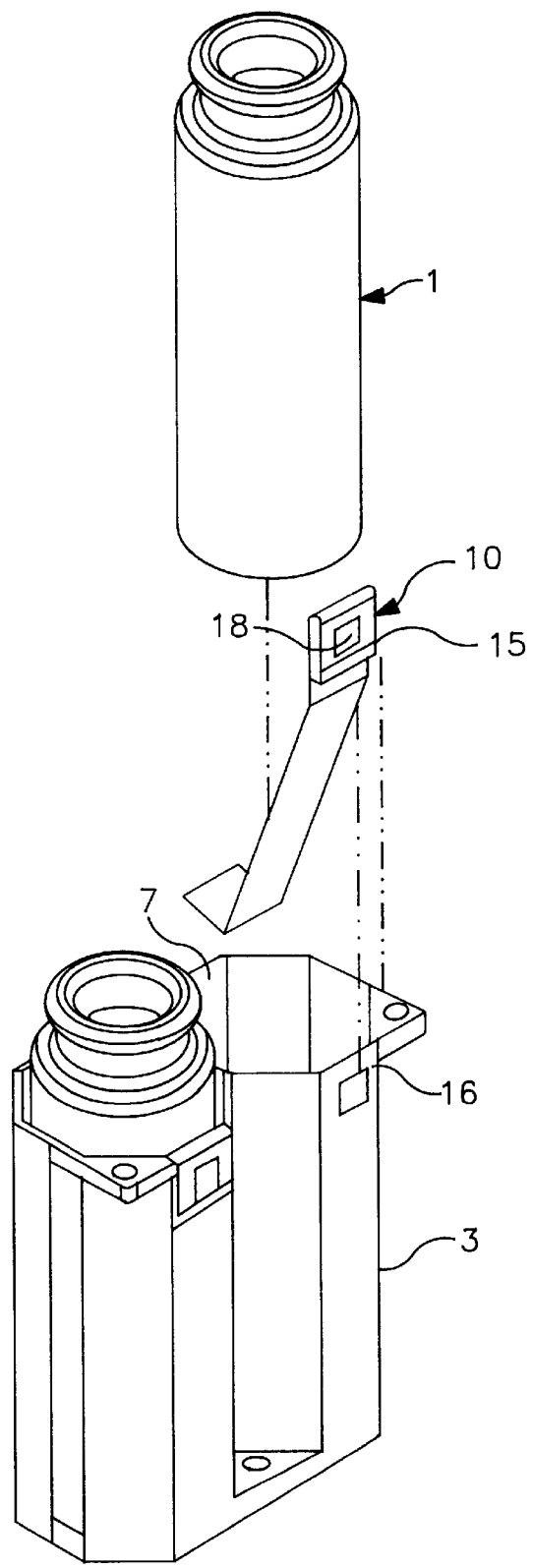
FIG. 3 is an exploded view of a part of the bottle holder of FIG. 2.

As can be seen in FIG. 3, an the exploded view of FIG. 2, within cavity 7 of bottle holder 3, a retaining clip 10 is provided for holding bottle 1 in place. Depending upon the type of microorganism to be detected, the rack can be moved back and forth within the incubating apparatus for agitating the media in the culture bottles to promote microorganism growth. For this reason it is desirable to have some type of retaining mechanism within the bottle holders to hold bottles in place during agitation. As can be seen in FIG. 3, in one embodiment a retaining clip 10 has a top U-shaped portion 15, which fits over a top portion 16 of the bottle holder.

Figure 4:
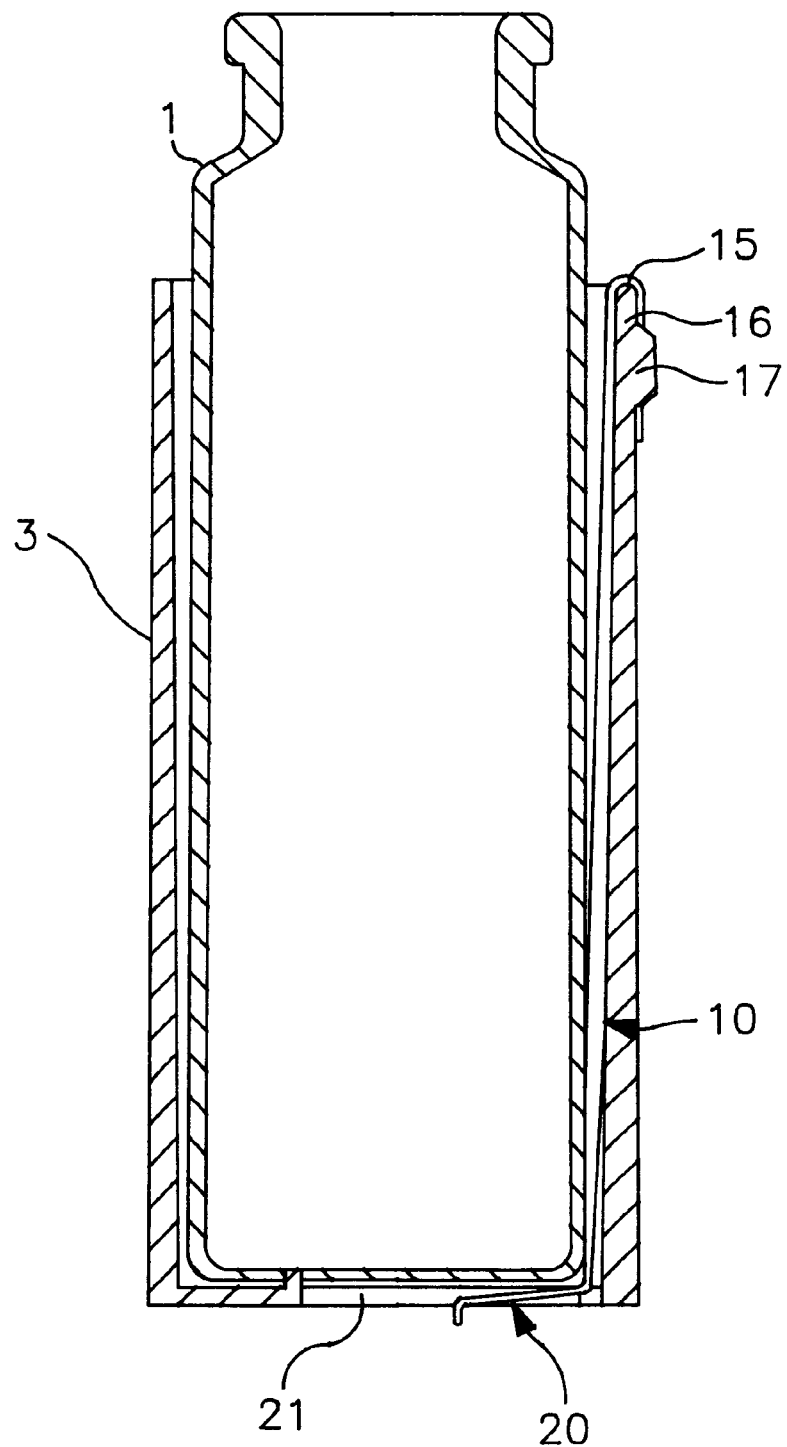
FIG. 4 is a cross sectional view across a bottle holder with bottle held therein.

As can be further seen in FIG. 4, retaining clip 10 has a top U-shaped portion 15 fitting over a top portion 16 of a wall of the bottle holder. A protrusion 17 on the top wall portion 16 fits through a hole 18 (see FIG. 3) in the retaining clip. of course, there are many other ways in which the retaining clip could be mounted on the bottle holder well known to those skilled in the art, such as with adhesives, welding, screws, etc. Reflecting leg portion 20 is also illustrated in FIG. 4.

Figure 5:
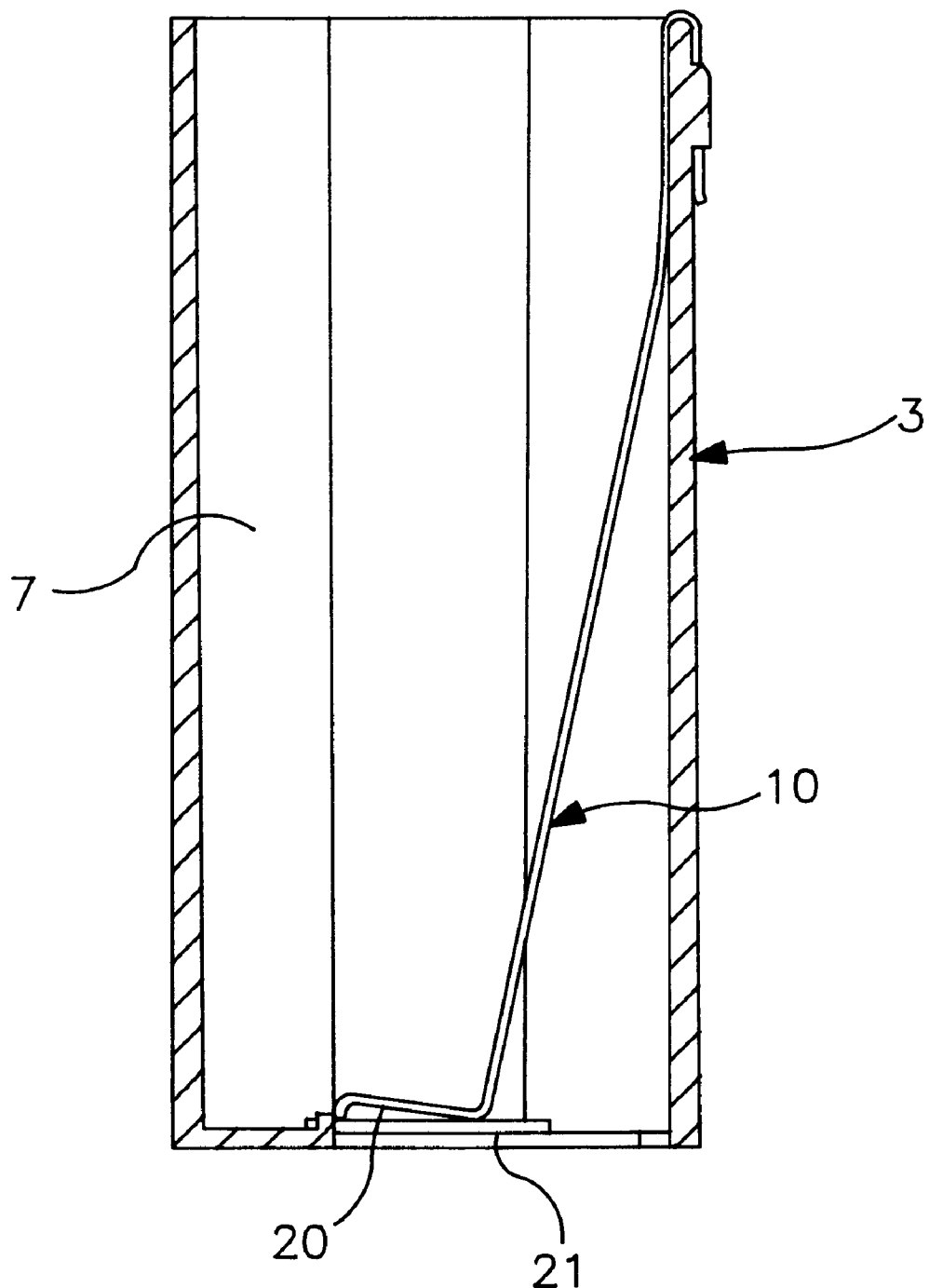
FIG. 5 is a cross sectional view of a bottle holder without a bottle therein.
Figure 6:
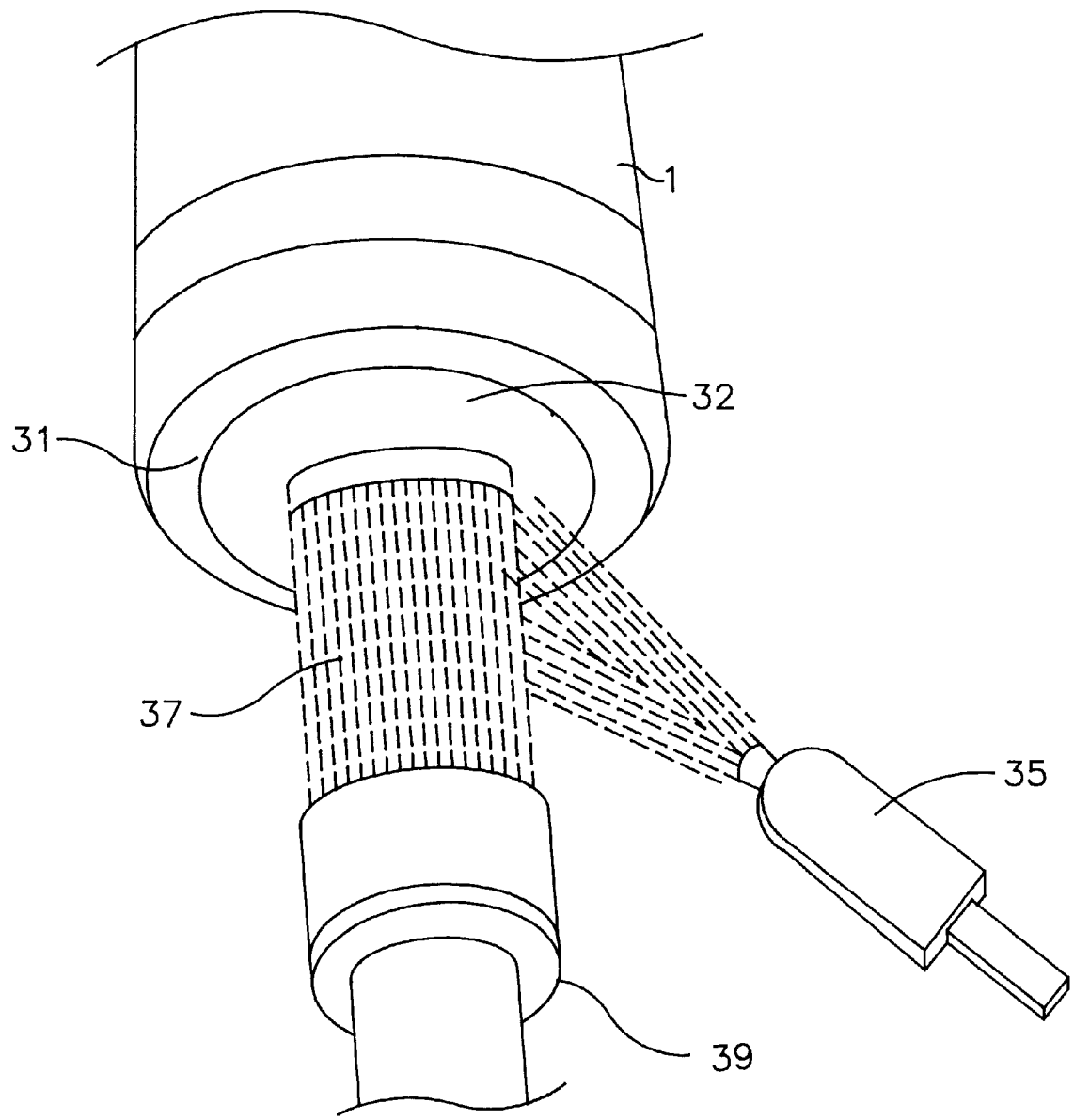
FIG. 6 is an illustration of a bottle bottom with light detector and emitter.

As is illustrated in FIG. 5, when a bottle is not held within the bottle holder, the retaining mechanism springs toward the center of the cavity 7 away from the inner wall. In this position, the reflecting leg portion 20 is in the middle of the bottom hole 21 of the bottle holder. When a bottle is in place, as in FIG. 4, hole 21 allows light from a light emitter to reflect from the surface of a sensor in the bottom of the bottle, which reflected light is detected by a light detector. This arrangement can better be seen in FIG. 6, where a bottle 1 has a transparent bottom surface 31 and a sensor 32 on the inside of the bottle adjacent the transparent bottom bottle surface. A light source 35 shines light onto the bottle's bottom surface and reflected light 37 from sensor 32 is received at light detector 39. If a bottle is not present in the bottle holder, as in FIG. 5, however, the light from the light detector will instead be reflected by light reflecting leg 20 (reflectance flag) of the retaining clip 10 and be detected by the light detector 39.

In operation, the retaining clip/reflectance flag has a reflective surface that reflects an amount of light greater than the amount of light reflected from a culture bottle. Thus, if the amount of light detected at the light detector is greater than a predetermined threshold, it is an indication of an empty bottle holder cavity. For the present invention, the reflecting surface of the retaining clip/reflectance flag must consistently provide a signal greater than that of the brightest bottle that might be used in the incubating apparatus.

And, the retaining clip must properly retain a culture bottle during agitation in the incubating apparatus.

Alternatively, the "reflecting" portion of the retaining clip could be provided with an absorbing material. In this embodiment, the amount of light reflected from the reflecting surface must always be less than the least reflective bottle. Thus, if the amount of light detected at the light detector is less than a particular predetermined threshold, than this is an indication of an empty bottle holder cavity. Also, the reflecting surface of the retaining clip could be provided with a fluorescence material that fluoresces when light from the light emitter impinges on the retaining clip. Such an arrangement could be used in conjunction with a culture bottle having a fluorescence sensor. The amount of fluorescence of the retaining clip would be set so as to always be greater or always be less than the fluorescence of the sensor in the bottles.

The retaining clip can have a further function of providing a signal when a bottle is not present in the bottle holder cavity, that can be used for detection of changes in LED brightness and/or photocell sensitivity (an automatic quality control check). By monitoring changes in the empty cell reflectance, changes to cell calibration can be measured. Compensation can be made for small changes, whereas for large changes, a cell could be taken out of service until it can be calibrated with standards. A microprocessor is used for determining changes in LED brightness or photocell sensitivity, such as a Motorola 688H11, or a similar 16 bit processor.

Previous calibration/quality control involved the insertion of calibration standards periodically to verify that the cells in the instrument are still in calibration. Because a single incubating/microorganism detecting apparatus can have hundreds of cells, each for holding a respective culture bottle, this type of calibration is an enormous time consuming task. For this reason, the automatic quality control of the present invention is very desirable.

The light emitting diode in the light source can be, for example, an AND180CRP, which can supply 4000 mcd. The current through the LED is controlled by a Rack Controller microprocessor. Initial factory calibration is performed using calibration standards. A table of LED current vs. A/D counts for several reflectance levels is created for the empty cell. For example, if it is assumed that the cell has been calibrated using a LED current of 8.4 mA, several reflectance values could be selected for use for auto-calibration and verification. The reflectance values of the calibration standards are a possible selection. The A/D counts associated with the reflectance are then determined, and the LED current is varied to get the desired A/D counts. The A/D counts and LED current measurements are stored for auto-calibration and verification.

Periodically, the rack controller will set the LED current to each of the values for the empty cell. The A/D counts measured will be compared to the counts in the table. Any changes in the cell (either the light output of the LED or the sensitivity of the detector circuit) will be detected by changes in the A/D counts. Small changes can easily be compensated for using standard techniques. As such, the need for periodic verification with calibration standards is eliminated. Changes beyond a predetermined threshold will render the cell unusable. Calibration with standards is desirable before such a cell is used again.

The material of the retaining clip can be almost anything that is within the proper range of rigidlity/flexibility, and that has a reflectance higher than the most reflective bottle that would be used in the incubating/detecting apparatus. Examples include Lexan, Styrene, Teflon and stainless steel, though many other polymers, metals and other materials could be used. Also, as an alternative, a second reflective material (e.g. reflective tape, a white non-gloss dot, a painted surface, a mirror, etc.) could be placed on the lower surface of an otherwise lesser reflecting retaining clip.

Of course, variations on the example disclosed above could be envisioned. For example, a coil spring could be utilized which extends to position a reflective plane in the beam of light from the light emitter, could be used. Or, a flexible planar element could naturally extend horizontally to intersect the beam of light when no bottle is present, but be bent out of the way when a bottle is inserted into the bottle holder. In fact, a non-movable reflective material could be positioned which is targeted by the beam of light once a bottle has been removed from the bottle holder.

Those skilled in the art, having the benefit of the teachings of the present invention as are hereinabove set forth, may effect numerous modifications thereto. It should be understood that these and other modifications lie within the scope of the present invention as set forth in the appended claims.

We claim:

1. An apparatus comprising:
   a light emitter;
   a light detector;
   a container holder for holding a container therein; and
   a reflective or fluorescent surface;
   wherein said light emitter is directed towards a bottom portion of said container holder such that when a container is present in said container holder, light from said light emitter reflects off of a reflective surface of the container, or causes a fluorescent surface to emit fluorescence, which in turn is received and detected by said light detector;
   and wherein only when a container is absent from said container holder, light from said light emitter reflects off of a reflective surface, or causes fluorescence to be emitted from a fluorescent surface, which in turn is received and detected by said light detector.

2. The apparatus of claim 1, wherein said reflective or fluorescent surface is of a higher reflectivity or fluorescence than a sensor in the container, such that a greater amount of light is received and detected by said light detector when a container is absent from said container holder.

3. The apparatus of claim 1, wherein said reflective or fluorescent surface is a biased and movable mechanism which acts to hold a container in place when the container is within the container holder.

4. The apparatus of claim 3, wherein said reflective or fluorescent surface is constructed so as to move to a position to reflect light or fluoresce due to light from said light detector when a container is absent from said container holder.

5. The apparatus of claim 4, wherein said reflective or fluorescent surface is a leaf spring attached to an upper portion of said container holder.

6. An apparatus comprising:
   a bottle holder for holding a bottle and having an aperture in a wall thereof;
   a retaining mechanism in said bottle holder;
   wherein said retaining mechanism retains a bottle within said bottle holder when a bottle is present therein;
   and wherein when a bottle is absent from said bottle holder, said retaining mechanism moves to be positioned at least in part adjacent said aperture of said bottle holder.

7. The apparatus of claim 6, wherein said retaining mechanism has a reflective or fluorescent surface on at least one wall thereof.

8. The apparatus of claim 7, wherein said reflective or fluorescent surface of the retaining mechanism is disposed immediately adjacent said bottle holder aperture when a bottle is absent from said bottle holder.

9. The apparatus of claim 6, wherein said bottle holder comprises a plurality of cavities for holding a plurality of bottles, each cavity having at least one aperture and a retaining mechanism therein.

10. An apparatus having at least one detecting cell, comprising:
   a light emitter;
   a light detector;
   a bottle holder for holding a bottle therein, said bottle holder comprising a reflector;
   wherein said light emitter is directed towards said bottle holder such that light from said light emitter reflects off of said reflector and is received and detected by said light detector, and wherein changes in an amount of said light detected by said light detector off of said reflector are used for calibrating said apparatus.

11. The apparatus of claim 10, wherein changes in the amount of said light from said reflector which are less than a predetermined amount are compensated for to bring the apparatus back into calibration, whereas changes greater than a predetermined amount cause the apparatus to be placed out of use.

12. The apparatus of claim 10, wherein said reflector is disposed within a cavity of said bottle holder and reflects light to said light detector when a bottle is absent from said bottle holder.

13. The apparatus of claim 10, wherein said reflector is constructed so as when a bottle is placed in said bottle holder, said reflector acts to hold the bottle in place.

14. An apparatus comprising:
   a container holder for holding a container therein;
   a light emitter for directing light towards said container holder;
   a light detector for detecting light reflected or fluoresced from a container within said container holder;
   a container retaining mechanism for retaining said container within said container holder, said retaining mechanism constructed so as to reflect or fluoresce light to be detected by said light detector; and
   a processor for processing light from said container and/or said retaining mechanism.

15. The apparatus of claim 14, wherein when no container is present in said container holder light is reflected or fluoresced from said retaining mechanism and is detected by said light detector, and said processor processes said light received and determines whether said apparatus is out of calibration.

16. The apparatus of claim 14, wherein said container is a culture bottle with a calorimetric and/or fluorescent sensor adjacent a transparent wall of said container, and wherein said processor processes changes in said sensor if microorganisms grow within a culture media in said container.

17. The apparatus of claim 14, wherein said light from said light emitter is infrared, visible, or ultraviolet light.

* * * * *